(12) United States Patent
Austria

(10) Patent No.: US 7,156,231 B1
(45) Date of Patent: *Jan. 2, 2007

(54) SHARP BLADE PROTECTION DEVICE

(76) Inventor: Georgene Austria, 5755 Valarie Ave., Woodland Hills, CA (US) 91367

( * ) Notice: Subject to any disclaimer, the term of this patent is extended or adjusted under 35 U.S.C. 154(b) by 0 days.

This patent is subject to a terminal disclaimer.

(21) Appl. No.: 11/164,061

(22) Filed: Nov. 9, 2005

Related U.S. Application Data

(63) Continuation of application No. 11/163,863, filed on Nov. 1, 2005.

(51) Int. Cl.
*B65D 85/00* (2006.01)
*A61B 17/32* (2006.01)

(52) U.S. Cl. .................. 206/355; 606/167; 30/335

(58) Field of Classification Search ............ 206/438, 206/363–366, 352–355; 606/167
See application file for complete search history.

(56) References Cited

U.S. PATENT DOCUMENTS

| | | | |
|---|---|---|---|
| 4,707,920 A | 11/1987 | Montgomery | 30/294 |
| 4,719,915 A | 1/1988 | Porat et al. | 128/305 |
| 4,735,202 A | 4/1988 | Williams | 128/305 |
| 5,071,426 A | 12/1991 | Dolgin et al. | 606/167 |
| 5,139,507 A | 8/1992 | Dolgin et al. | 606/167 |
| 5,207,696 A | 5/1993 | Matwijcow | 606/167 |
| 5,250,064 A | 10/1993 | Schneider | 606/167 |
| 5,275,606 A | 1/1994 | Abidin et al. | 606/167 |
| 5,330,492 A | 7/1994 | Haugen | 606/167 |
| 5,330,493 A | 7/1994 | Haining | 606/181 |
| 5,330,494 A | 7/1994 | van der Westhuizen | 606/167 |
| 5,417,704 A | 5/1995 | Wonderly | 606/167 |
| 5,431,672 A | 7/1995 | Cote et al. | 606/167 |
| 5,478,346 A | 12/1995 | Capewell | 606/167 |
| 5,527,329 A | 6/1996 | Gharibian | 606/167 |
| 5,556,409 A | 9/1996 | Haining | 606/181 |
| 5,569,281 A | 10/1996 | Abidin et al. | 606/167 |
| 5,571,127 A | 11/1996 | DeCampli | 606/167 |
| 5,571,128 A | 11/1996 | Shapiro | 606/167 |
| 5,620,454 A | 4/1997 | Pierce et al. | 606/167 |
| 5,662,669 A | 9/1997 | Abidin et al. | 606/167 |
| 5,676,677 A | 10/1997 | Landis et al. | 606/167 |
| 5,730,751 A | 3/1998 | Dillon et al. | 606/167 |
| 5,741,289 A | 4/1998 | Jolly et al. | 606/181 |
| 5,752,968 A | 5/1998 | Jolly et al. | 606/167 |
| 5,792,162 A | 8/1998 | Jolly et al. | 606/167 |
| 5,827,309 A | 10/1998 | Jolly et al. | 606/167 |

(Continued)

*Primary Examiner*—Jila M. Mohandesi
(74) *Attorney, Agent, or Firm*—Law Office of Ken Dallara; Ken Dallara

(57) ABSTRACT

A sharps blade protection device is disclosed that adapts to currently used scalpel handles but uniquely is also usable with other existing styles of sharps including kitchen and hobby knives. This invention is adaptable over a broad range of sharps devices enabling users of many different sharps to be protected during and after use. The device is designed so that the user can easily insert and remove the sharp so that training of use is minimized if needed at all. The device is usable with a single hand, and both left handed or right handed operators are able to use all of the benefits of this device with equal ease. Device can include a member whereby it removes the tang portion of a surgical scalpel blade from the holder on the scalpel and places it onto a retention post, where it remains until the blade is safety removed from the handle by a movement of the blade guard. This device is designed to be reusable and cleanable but is capable of inexpensive manufacturing leading to it's use as a disposable device.

22 Claims, 15 Drawing Sheets

U.S. PATENT DOCUMENTS

| | | |
|---|---|---|
| 5,843,107 A | 12/1998 | Landis et al. ................ 606/167 |
| 5,868,771 A | 2/1999 | Herbert et al. ............... 606/167 |
| 5,908,432 A | 6/1999 | Pan ............................ 606/167 |
| 5,938,676 A | 8/1999 | Cohn et al. .................. 606/167 |
| 5,941,892 A | 8/1999 | Cohn et al. .................. 606/167 |
| 6,022,364 A | 2/2000 | Flumene et al. ............ 606/166 |
| 6,589,258 B1 | 7/2003 | Pilo et al. .................... 606/167 |
| 6,626,925 B1 | 9/2003 | Newman et al. ............. 606/167 |
| 6,629,985 B1 | 10/2003 | Kiehne ....................... 606/167 |
| 6,757,977 B1 | 7/2004 | Dambal et al. ............... 30/162 |
| 2002/0133952 A1 | 9/2002 | Kenny ......................... 30/151 |
| 2004/0226175 A1 | 11/2004 | Ping ............................ 30/340 |
| 2004/0244204 A1 | 12/2004 | Elsener-Zehnder et al. ... 30/151 |
| 2005/0119680 A1 | 6/2005 | Dykes ........................ 606/167 |
| 2005/0138816 A1 | 6/2005 | Ping ............................ 30/160 |

FIGURE 1
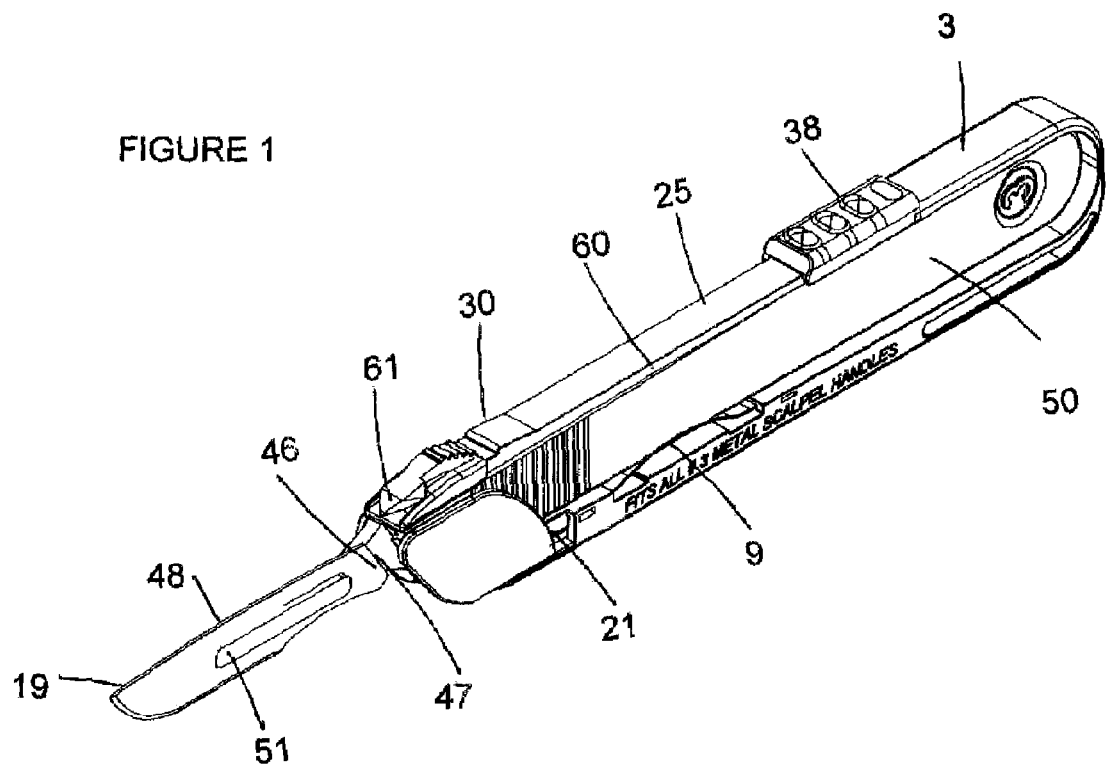
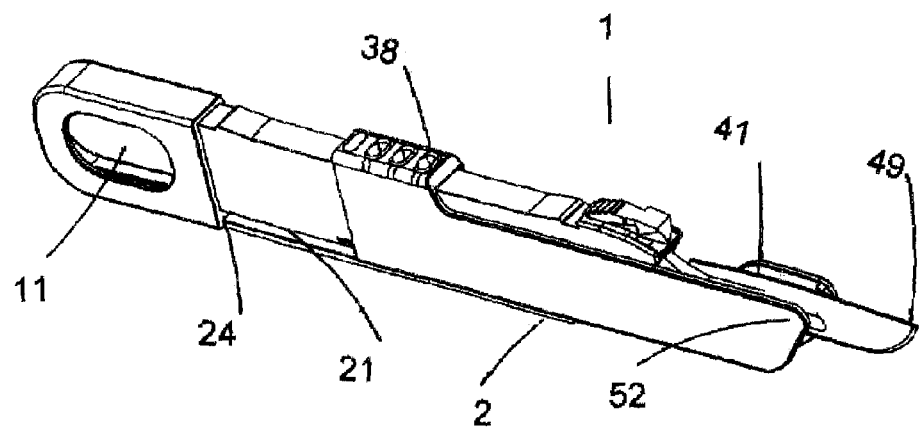

FIGURE 3
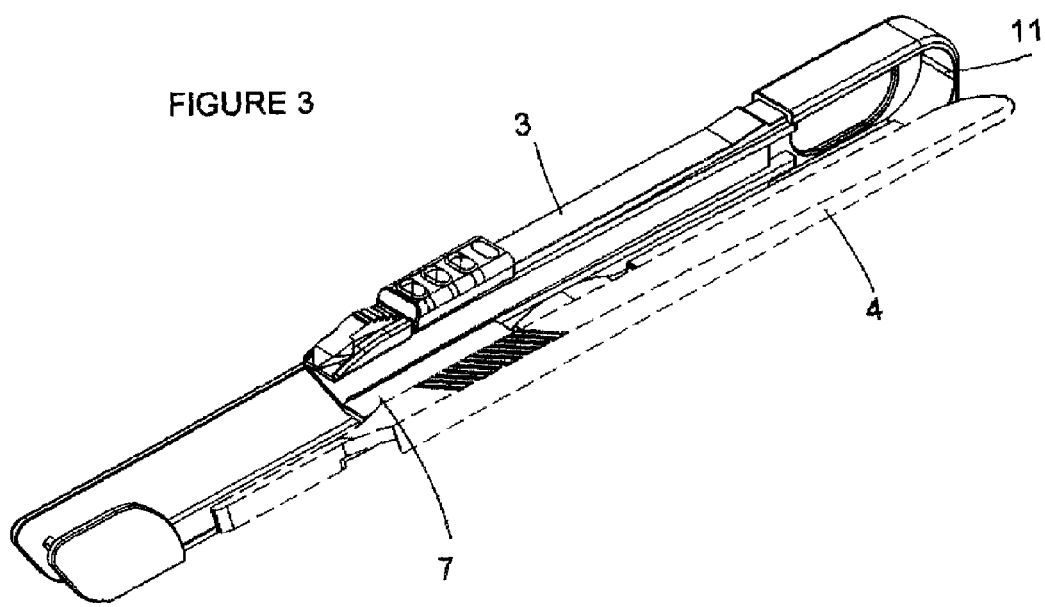
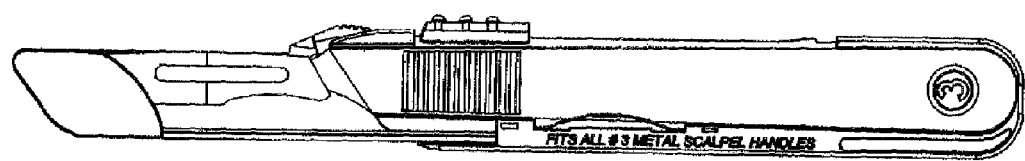

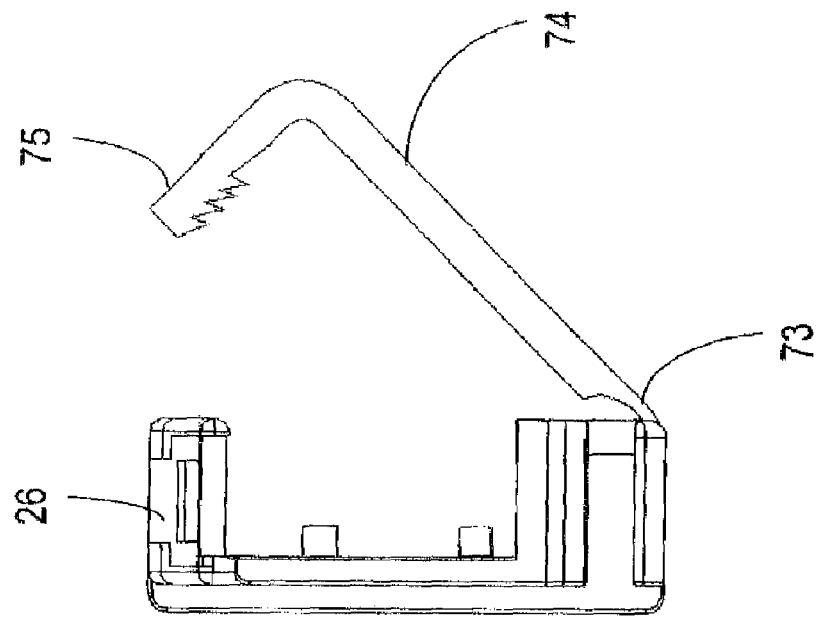
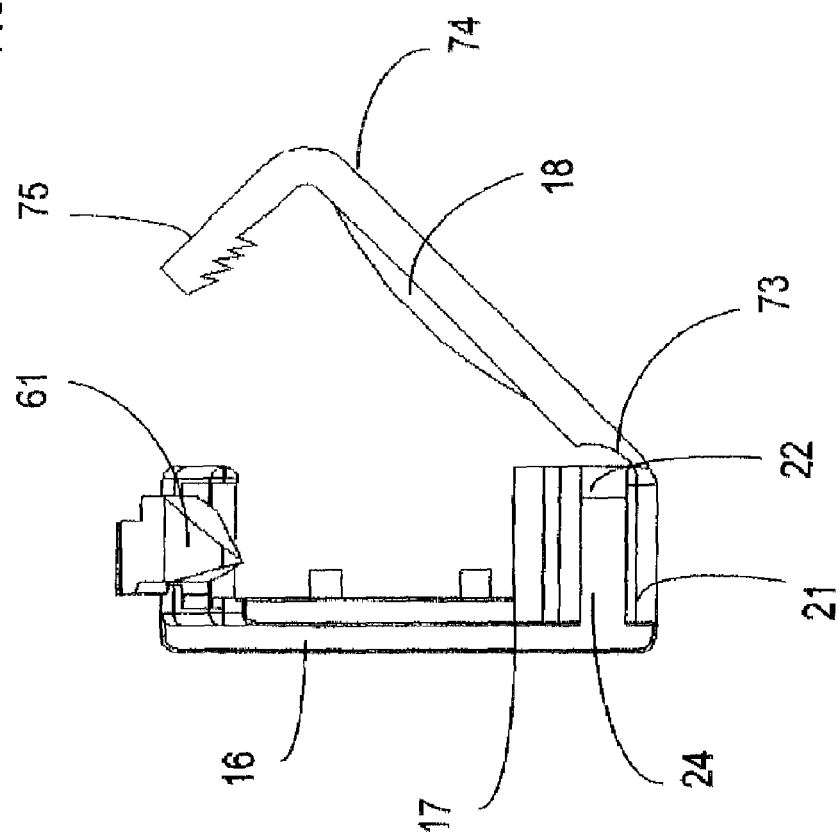
FIGURE 11

SHARP BLADE PROTECTION DEVICE

CONTINUITY DATA

This application is a continuation of application 11/163,863 filed on Nov. 1, 2005, now pending.

FIELD OF INVENTION

This invention applies to the field of protecting users and those associated with users, of sharp objects such as those used in the surgical or medical applications. This invention is applicable to other such sharp devices such as paring or boning knives with straight blades.

BACKGROUND OF INVENTION

There are many industries and applications where sharp knives are used. Applications from surgery to meat-cutting to recreational fishing all use knives with very sharp blades and equally sharp points. Each year many users accidentally slice or puncture themselves with sharp instruments either during use, during transfer from one person to another or from inadvertent misplacement of sharps in potentially dangerous locations. This is especially dangerous in the medical arena, as potentially fatal diseases can be spread through accidental contact with sharps. Emergency Rooms are battlegrounds compared to the operating rooms where quick action amongst many people are required to save lives. Sharp protection is a must and must be easy to operate. Prior art is replete with many different style of devices that act to cover sharp blades.

There are 5 main types of prior art that exists to prevent users from accidental contact with sharp blades. The 5 areas involve devices where 1) the sharp is retracted into the body of the device, 2) where the device is a disposable or single use application, where the entire sharp with the handle is not reused, 3) a device that moves in a non-linear fashion to cover the blade while it is not in use, 4) those devices which remove a detachable blade from the handle of the device. and 5) other devices that use non-traditional or devices specific sharp handles and blades and a cover that travels in a linear fashion over the sharp.

In the first arena of prior art, patents have been granted for devices mainly in the medical field. The basic premise for this group of patents is that the blade is extended from and retracted back into, the handle of the device. There is usually one handed operation of these devices, but the Shapiro U.S. Pat. No. 5,571,128 issued on Nov. 5, 1996 discloses a device that requires "rotary and longitudinal movement of the handle" to move the surgical element. That extra step of motion can be difficult if the surgeons hands are busy holding or manipulating another device. Most patents use devices that are similar in shape to existing scalpels but are machined or molded in such a manner to create a hollow in the body of the scalpel to hold serve as a chamber to store the blade while not in use. The Dillion et al U.S. Pat. No. 5,730,751 and the Cote et al U.S. Pat. No. 5,431,672 detail this style of retracting blade into the body prior art. Dillion provides for "an inoperative location within the handle" and Cote states that the blade is slid from an "intermediate position where the blade is within the handle". Both Cote and Dillion provide for the location of the triggering mechanism to retract the blade is nearest the distal or blade end of the device. Cote discloses the triggering mechanism on the side of the handle which could disturb the surgeon as that is the natural position of the surgeons hand during use and possibly hinder the operation of the scalpel should it be used in a tight surgical location such as under the arm or in persons with layers of fat, where the scalpel is often used past the coetaneous layers of the body. Both Cote and Dillion function only with their respective blades and handles are not transferable to current scalpels in use. There are also issues present that would make the sterilization after use of these devices to be difficult if possible at all.

The second arena of prior art involves the use of single use blades and handles. There are three main styles where the either the blade is retracted into the body, a shield is produced covering the blade or there is a separable device that is used to cover the blade. In the first style, Dambal et al in U.S. Pat. No. 6,757,977 issued on Jul. 6, 2004, Haining in U.S. Pat. No. 5,330,493 issued on Jul. 19, 1994 and U.S. Pat. No. 5,556,409 issued on Sep. 17, 1996, all disclose devices where the blade is first extended for a single use and then is withdrawn into the body and some mechanism will prevent the blade from being extended in the future. Thus making this device safe for disposal after a single use. While Dambal and Haining uses a manual method, thumb power, to retract the blade, Flumene et al in U.S. Pat. No. 6,022,364 issued on Feb. 8, 2000, is "operated through an elastic returns means". The second style involves the uses of a shield that moves over a stationary blade. Wonderley in U.S. Pat. No. 5,417,704 issued on May 23,1995, discloses "a blade carried by the handle adjacent one end thereof and a guard movably mounted to the handle for sliding movement relative to the handle between a protective position covering the blade and a retracted position exposing the blade." Where Wonderley discloses a manual operation to move the shield into the desired position, Pilo et al in U.S. Pat. No. 6,589,258 issued on Jul. 8, 2003 discloses the use of an "elastic return elements to bring the blade back into the retracted inoperative position". The third style as disclosed by Williams in U.S. Pat. No. 4,735,202 issued on Apr. 5, 1988, uses a separable shield device on a round handled scalpel that is removed and remounted after use. All of styles mentioned in this section involve the use of unique surgical handles and blades which are disposed of after use. This is an expensive alternative as the majority of the cost of a normally used scalpel is in the high precision surgically ground blade. It is not economically justifiable to use this method when medical costs are escalating very rapidly.

The third arena of sharps protection involve the use of a guard that moves to cover the sharp but does so in a non-linear path or motion. Landis et al in U.S. Pat. No. 5,843,107 issued on Dec. 1, 1998 and Schneider in U.S. Pat. No. 5,250,064 issued on Oct. 5, 1993 disclose a shield that is actuated by the surgeon's thumb, whereby a protective member is lifted away from the sharp during use. This presents several issues; as the surgeon's thumb is not naturally located above the blade during or prior to use, the cover would present sight issues as it would be in the line of sight of the surgeon during use, the cover would prohibit the use of the blade subcutaneously as is required in certain surgical procedures or involving persons who are overweight and it requires that the surgeon pay attention to something other than the patient as the surgeon must be aware of holding the shield in position. Though both of these patents allow for use on existing sharps, it involves the placement of the devices next to the sharp where there exist a large chance of accidental puncture. Capewell in U.S. Pat. No. 5,478,346 issued on Dec. 26, 1995 also discloses a sharps guard but here there is "a blade guard attached to the scalpel by a frangible tether". Capewell uses a non-standard scalpel for this application and requires the user to move their fingers next to the sharp to operate this guard. This guard also contains the problems associated with the Landis and Schneider patents as well.

The fourth arena of the prior art involves the use of devices whereby the sharp is attached to and then removed from the handle. In one group, there are those devices where the sharp is directly attached to the handle and another group contains devices where the sharp is placed into a cartridge which is then placed upon the handle. Both groups involve handling of the sharp prior to it's inclusion into some protective cover, increasing the chance of accidental puncture. In the first group, Herbert et al in U.S. Pat. No. 5,868,771 issued on Feb. 9, 1999, Newman et al in U.S. Pat. No. 6,626,925 issued on Sep. 30, 2003 and van der Westhuizen et al in U.S. Pat. No. 5,330,494 disclose the procedure of attaching the sharp to the handle and then attaching a sliding blade guard. Once the sharp is used, the blade can be removed along with the guard. Herbert uses existing style surgical handles, while van der Westhuizen and Newman use a unique handle that is modified at the distal end of the handle nearest the sharp, to receive the guard. Both devices require the use to load the sharps device onto the handle, requiring the unguarded sharp to be handled by those that the device is designed to protect, and often those people are wearing gloves which will reduce tactile feel. In a different approach disclosed by Noack in U.S. Pat. No. 5,312,429 issued on May 17, 1994, where a unique blade with an opposed tang is removed by sliding blade release element when the element is slid down the handle toward the sharp. This is a two handed operation involving two separate pieces. In the sliding of the element, if one's hand slips from the element it would be certainly by cut by the exposed blade. Also the blade is without direction or restraint when released from it's location on the handle. It could fly anywhere in the operating room as there is tension built up between the tang of the blade and the rest of the blade that was forced over the post on the handle. Another adaptation of this concept is found the series of patents from Jolly et al, U.S. Pat. Nos. 5,827,309, 5,752,968 and 5,792,162 issued Oct. 27, 1998, May 19, 1998 and Aug. 11, 1998 respectively. These Jolly patents show a blade remover which first removes the tang of the blade from the post into a notch on the sliding guard. Then '968 discloses that "guard 30 can be advanced distally to force blade 50 from blade carrier". The built in stresses mentioned above are now increased with a forcible removal of the blade with the sliding guard, increasing the chance for the blade to misdirected about the operating room. In the second group, Gharibian in U.S. Pat. No. 5,527,329 issued on Jun. 18, 1996 and Cohn et al in U.S. Pat. No. 5,938,676 issued on Aug. 17, 1999 disclose the use of a cartridge system whereby the sharp is placed into a cartridge which is then encased by a guard prior to it's placement onto the handle. This operation is safer as the sharp is guarded during assembly but creates a situation as each discloses a unique handle designed to receive the cartridges and shields. Cohn et al in U.S. Pat. No. 5,941,892 issued on Aug. 24, 1999 combines prior art by incorporating the cartridge concept that is "removably retained within the cavity" in the handle. This is a safe alternative but uses unique handles. All of the prior art in this section requires the use of two hands to safely operate the device which is at odds with current FDA compliance rules.

In the last arena of prior art, a guard is placed around a stationery blade. There is nothing unique about the concept, and it's application can be seen from the simple to the complex. In simple application of this concept, Patent Applications US2004/0244204 to Elsner-Zehnder et al and US2002/0133952 to Kenny, disclose blade guards whereby the knife is held in place and a guard is placed onto the knife. These applications are not surgically based but neither is the invention limited to medical applications. More complex applications of the concept are found in Abidin et al in U.S. Pat. No. 5,662,669 issued on Sep. 2, 1997 and U.S. Pat. No. 5,569,281 issued on Oct. 29, 1996, Jolly et al in U.S. Pat. No. 5,741,289 issued on Apr. 21, 1998, Matwijcow in U.S. Pat. No. 5,207,696 and Dolgin et al in U.S. Pat. No. 5,071,426 issued on Dec. 10, 1991. Matwijcow discloses a rack and pinion system for movement of the guard over the blade which causes a reverse sequence of logic, as the user needs to pull back to move the guard forward. This could be confusing in the fast paced operating room where several different type of devices might be used at once. Dolgin also uses a "linkage system" to extend the blade guard "over a substantially greater distance than the distance which the surgeon's fingers move in operating the actuating mechanism". This is unnecessarily complex and expensive concept using unique handles which requires manual loading of the blades onto the handle. Jolly provides for both linear actuation of the guard along with a rotational movement of the guard and blade away from the handle for cleaning purposes. This device is complex and expensive to manufacture and use. The Abidin '281 patent discloses a guard which "comprises an inverted U-shaped channel member telescopically mounted within the hollow handle for sliding movement therein". It is held in position by exposed an exposed pin which would be in the way of the surgeon's hands and could be accidentally triggered to move at the improper time. This device is also not usable with currently used scalpels and it requires a unique handle. Abidin '669 is another internally guided blade guard with a unique handle. But this patent also discloses in column 10 line 11, that it does not work with conventional scalpel blades. '669 does combine a blade guard and a blade ejector, but FIG. 36 details the need for two handed operation to remove the blade. FIG. 45 and FIG. 48 show that the blade is not restrained after it is removed from the handle, and as described above, there is a considerable amount of tension on the blade. The disclosure details the added tension as the guard actually pushes the blade off of the post upon which it is attached. There is nothing to restrain the loose blade. An unrestrained blade could fly off anywhere in the operating room and this is not a safe method of removal. '669 also discloses in FIG. 32 the complicated way of attaching the blade with two small pins, which would be very difficult with gloved hands in a hurried operating room. FIG. 13D of '669 shows the user sliding the guard forward using their forefinger, which would present an obvious problem should the guard become slippery due to bodily fluids, and the users finger slips from the guard onto the exposed blade.

There is a need to preclude the problems associated with the prior art and the current state of technology in this field. It would be preferable to produce a device that would provide current users with a device that would improve upon some of the shortcomings of the prior art. It would be advantageous that the prior art would be able to produce a device that would cover sharps with a minimal of effort, with only a single hand to operate such a device, and that the device be usable over a wide range of existing sharps. Industry has set standards for their equipment and it would be desirable to have a device that fits their standard equipment, rather than adapt to new equipment. Sharps users, especially surgeons, are used to the fit, form and feel of their tools of the trade, and are reticent to change. It is well practiced in the medical field, that metal sharps handles are used because they possess a certain weight and balance that plastic handles have a hard time replicating. Industry needs to adapt protections to currently used sharps, as new device are usually met with skepticism and doubt, and are thus not used. Industry does not want to carry duplicative inventories of many similar products because they do not work with one another.

It would be desirable for an invention that would be simple in design and yet adaptable to different types of sharps. It would be desirable to have this device be made in such a manner that it would be reusable and manufacturable in great quantities, lower product costs while assuring repetitive quality throughout the devices could even make this product disposable after a single use. It would be desirable to have the device made of autoclavable plastic or metal and designed so that it will not have any hidden recesses or other cavities that would trap harmful bacteria precluding the chance that it could be autoclavable. It would be advantageous that a blade remover apparatus be designed where only a single hand is needed for operation and where the blade is held rather than just pushed off the blade post creating a more secure environment.

BRIEF SUMMARY OF THE INVENTION

Accordingly, it is the goal of this invention to create a sharps protection device that has the aforementioned characteristics of simplicity, protection, adaptability to current uses and safety. It is an object of this invention to create a device that will protect both the user of the sharp as well as the person who comes in accidental contact with misplaced sharps, and for the person to which the sharp is transferred.

It is an object of this invention to create a device that is operable with a single hand and allows for the user to be either left or right handed to operate the device. The user must be able to retract or extend the sharps guard and be able to remove the sharp from the handle if that option is available to the user with the particular sharp.

It is an object of this invention to create a device that does not interfere with the normal operation of sharps and that it does not substantially change the feel of the sharp. The device does not contain any impediments that would prevent the user from using the device as they would the bare tool without the device.

It is an object of this invention to create a device that is rapidly interchangeable between a wide range of sharp's handles and blades. The device must be simple to use and maintain. Users must be able to disassemble, clean, and reassemble in a matter of moments, while using gloved hands with reduced tactile feel. The device must have no small or intricate parts which would preclude the quick assembly of the device.

It is an object of this invention to create a device which adapts to current state of the art devices, reducing the need for training, evaluating and maintaining multiple inventories of devices and sharps.

It is an object of this invention to create a device which has positive stops, including tactual and auditory signals, indicating the relative position of the guard, either in retraction or extension of the sharps protection device.

It is an object of this invention to create a device that does not involve placing of the protective device in such a manner that actually increases the likelihood of accidental contact with the sharp. The user should be able to use the device immediately "out of the box" without having to add guarding or assemble cartridges prior to safe use.

It is an object of this invention to create a device that will provide for safe removal of the sharp from the sharps holder without the possibility unknown trajectories and while using only a single hand for the operation.

It would be desirable to create a device which is cleanable without internal voids, sharp corners, chambers or holes which trap unsanitary material precluding the ability to easily clean, sanitize or reuse the device.

DESCRIPTION OF DRAWINGS

In FIG. 1 shows the device with hammer from a frontal oblique view in the closed position with a scalpel inserted for clarity.

FIG. 11 shows a front view of the guard showing the cleat in the open position, the two views showing the guard with and without the hammer detailing the hinge portion.

DETAILED DESCRIPTION OF INVENTION THROUGH DRAWINGS

Figure 2:
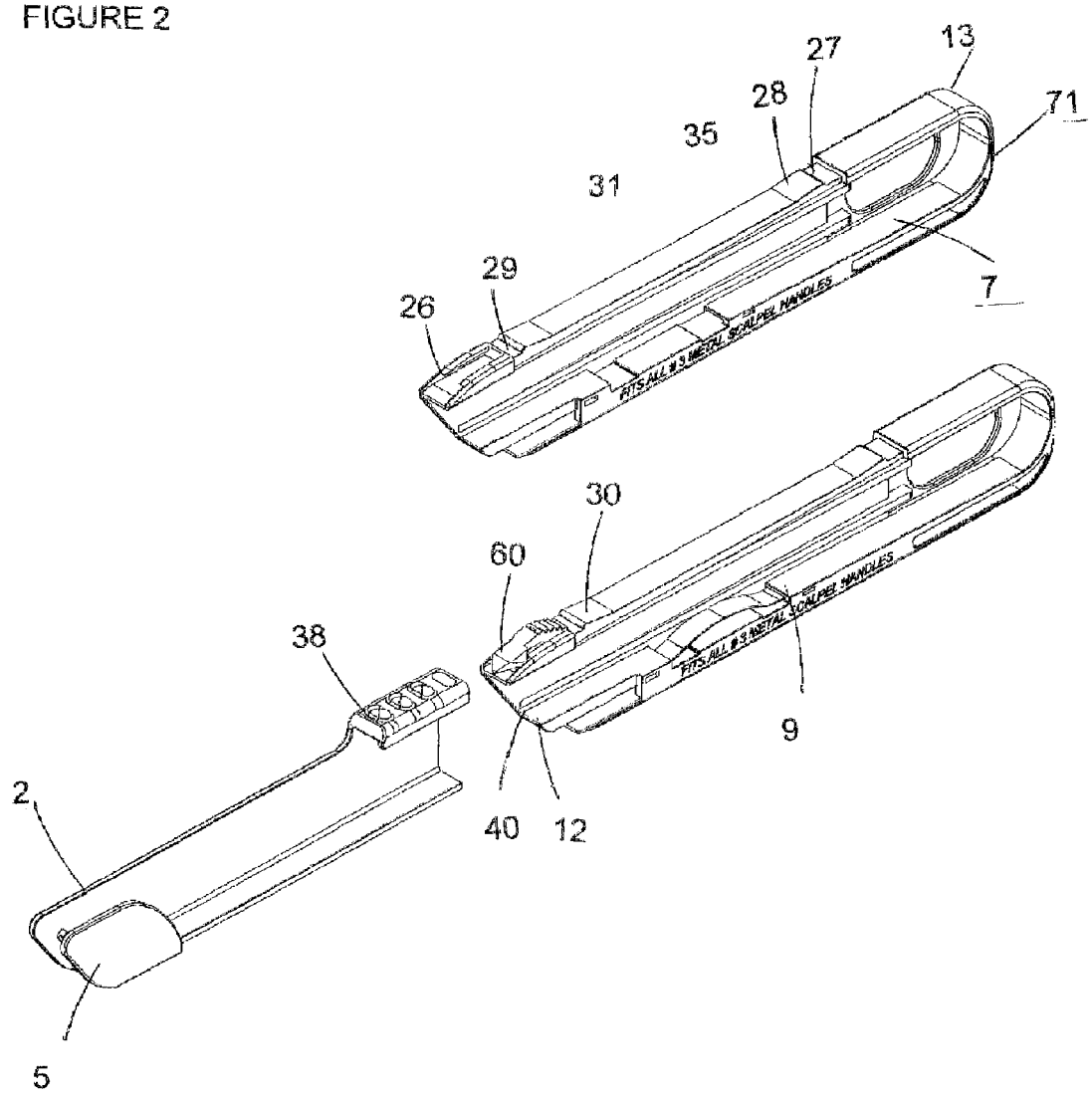
In FIG. 2, shows the device with the hammer from a frontal oblique view in the open position with a scalpel omitted for clarity In FIG. 3 details the method for inserting a scalpel into the device.

The following detailed description of the drawing is provided to show the enablement of the aforementioned principles in connection with this invention as it applies to the medical field, where surgeons, nurses and operating room personnel, as well as emergency medical technicians and paramedics in the field, need protection from accidental puncture or lacerations from unguarded scalpel blades. This is but one enablement of this invention as this invention is applicable to sharp instruments such as paring knives, used in the field and in the home, or industrial blades, such as X-Acto style of knives.

Figure 8:
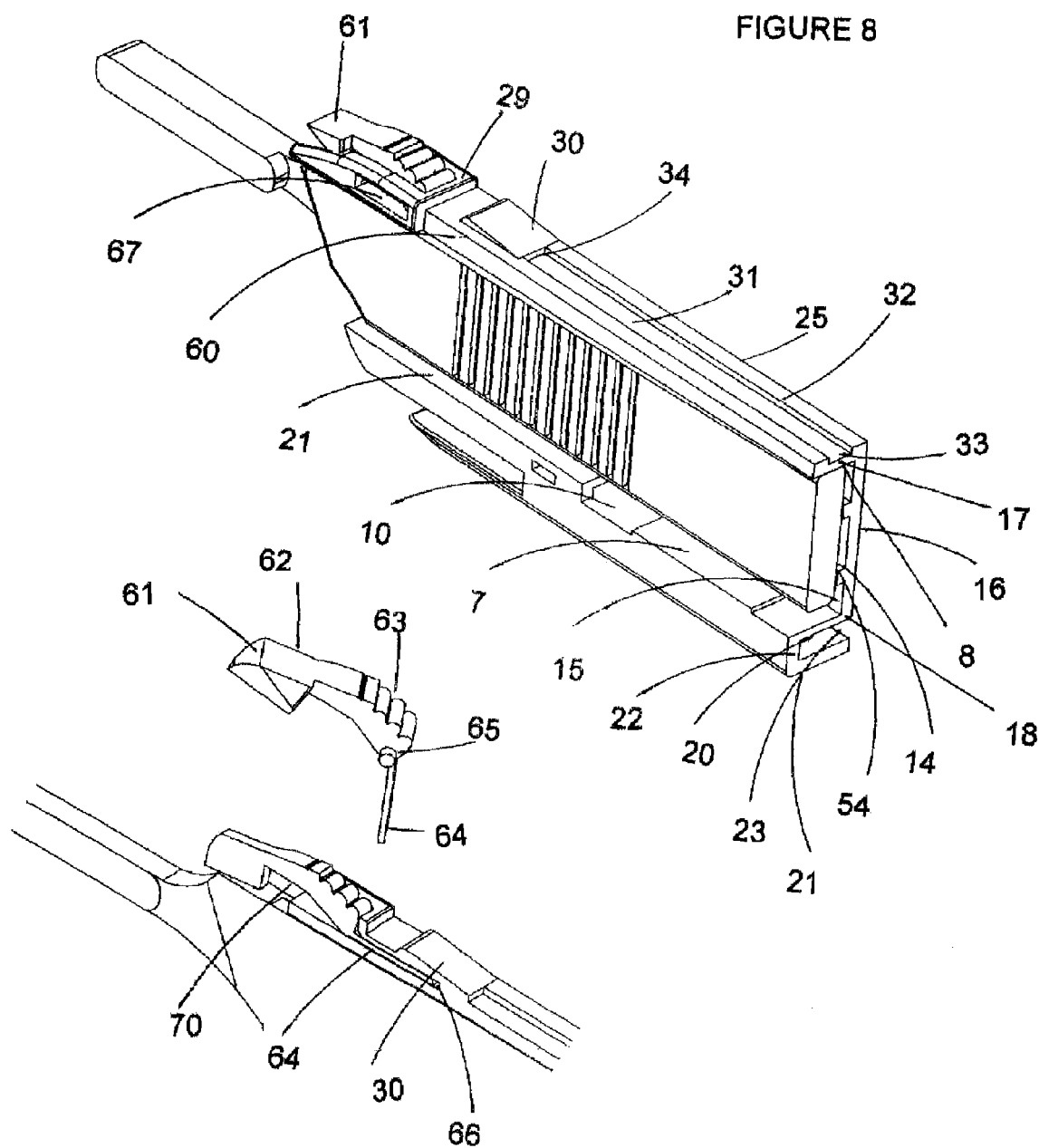
FIG. 8 is a half view from a rear oblique angle detailing the rail and the position of the handle in the device.

FIG. 1 shows device 1 that is an assembly of guard 2 and body 3. The material used in this example of best mode is an autoclavable moldable plastic such as Nylon. In this instance, this device is designed for use with #3 scalpel handle and that scalpel 4 is shown installed into body 3 and guard 2 with tip guard 5 is shown covering the exposed blade. FIG. 3 details guard 2 is composed of lateral blade protection wall 52, sliding engagement member 53, linear travel guide block 38 and tip guard 5. FIG. 8 details body 3 is the part of the device that holds the sharp's handle in place and provide interface for the sliding of guard 2. Body 3 has an front side where the handle is loaded and a rear side. Body 3 is an object that has a major opening defined by a rear wall 14, having an interior side 15, an exterior side 16 and linear travel rail 25, having an upper rail 17 and lower rail 18 perpendicularly attached to the perimeter of rear wall 14 along the latitudinal axis of wall 14, having curved back wall 19 perpendicularly attached to the perimeter of rear wall 14 along the longitudinal axis of wall 14, proscribed about open front end 12 and an enclosed rear end 13. Enclosed rear end 13 is defined as that part of body 3 aft of sliding slot termination wall 24 including curved back wall 19 and escapement hole 11. Enclosed rear end 13 can be adapted to accept longer handles by removing vertical wall 71, section of curved back wall 19, perpendicular to rear wall 14 and attaching cleat 81 should additional forces by necessary to secure the handle into body 3.

Open front end 12 is defined as having a sloped entry cutback angle 40 which is congruent to angle 39 found on scalpels and can be adapted to other knives or stock angles. This cutback angle 40 enables the user to maintain proper angles during use of the scalpel and will not impinge on the users range of motion. The interior dimensions of body 3 in this example of best mode is consistent with standard accepted scalpel size, #3 scalpel handle is shown by example only and does not limit the size or scope of this invention. Scalpel handle's will maintain contact with the interior surface of curved back wall 19, lower shelf 7 and upper shelf 8. Aiding in the holding of the scalpel's handle in the correct position are positioning means 54. In this invention, ribs are used which taper slightly decreasing in height as ribs 54 approach open end 12. Linear slide guide 20 has three sides defined by lower rail 18, lower slide wall 21 and slot wall 22, In this invention, the open side of guide 23 is along exterior wall 18 shown in FIG. 1. Open side 23 could be opposite of exterior 18 with the opening coinciding with the major opening defined supra. Guard 2 in the open or rear position would cover the sharps handle should open side 23 face in the major opening.

Figure 9:
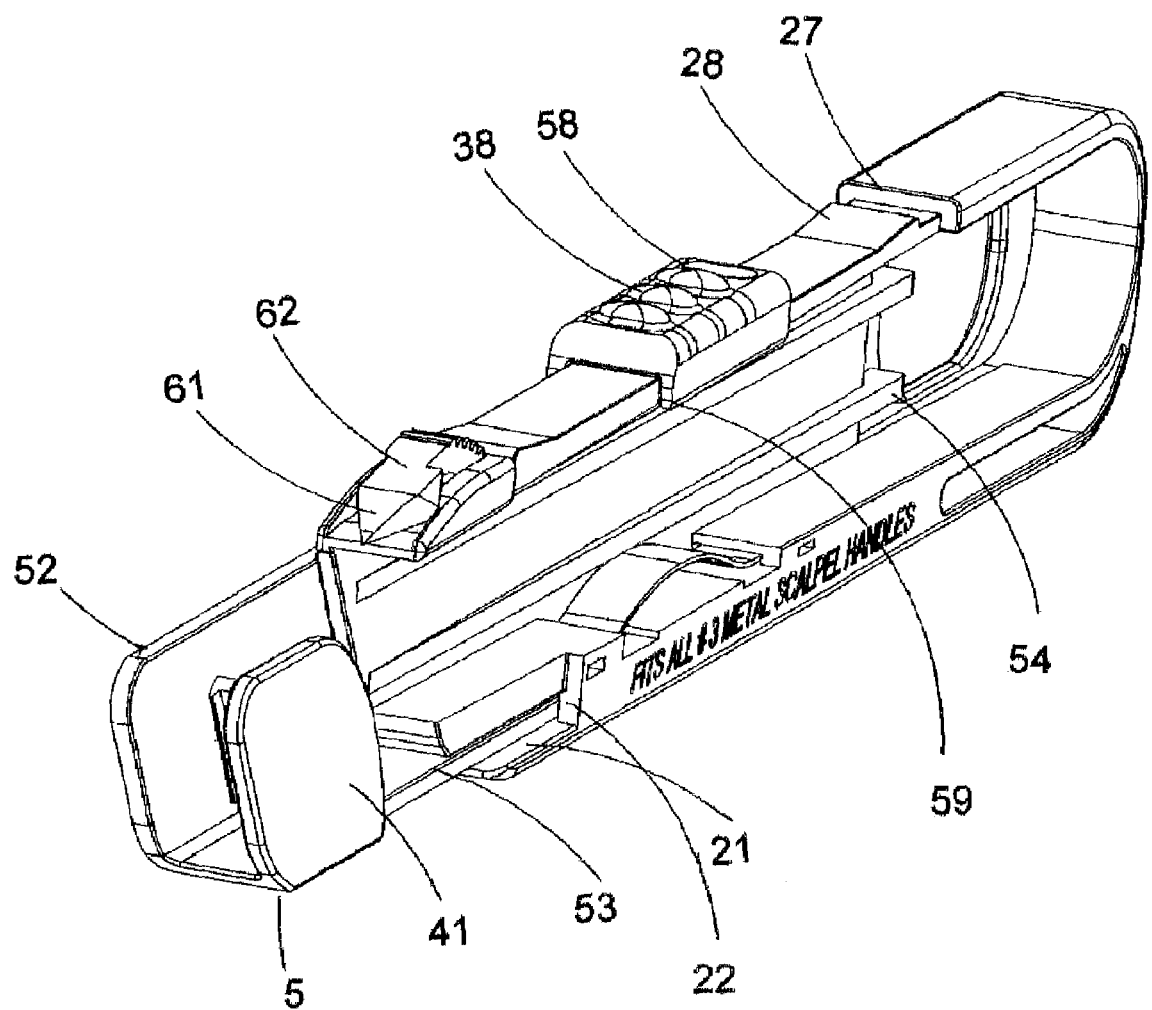
FIG. 9 shows the motion of the hammer through it's range of motion.

Linear slide guide 20 terminates at sliding slot termination wall 24 near rear end 13 at a point that will facilitate the entire retraction of guard 2 in the open position. Linear slide guide 20 extends through front end 12 enabling guard 2 to have positive contact with lower slide wall 21 through it's operating range. Slot wall 22 terminates at a point near front end 12, at a point that facilitates tip guard 5 in the retracted position as seen in FIG. 9.

Rear wall 14 also contains escapement hole 111 located at enclosed rear end 13. Escapement hole 11 is oval in shape similar to the users pad of their forefinger, but this does not preclude other shaped opening that would still facilitate the required purposed of hole 11.

Figure 4:
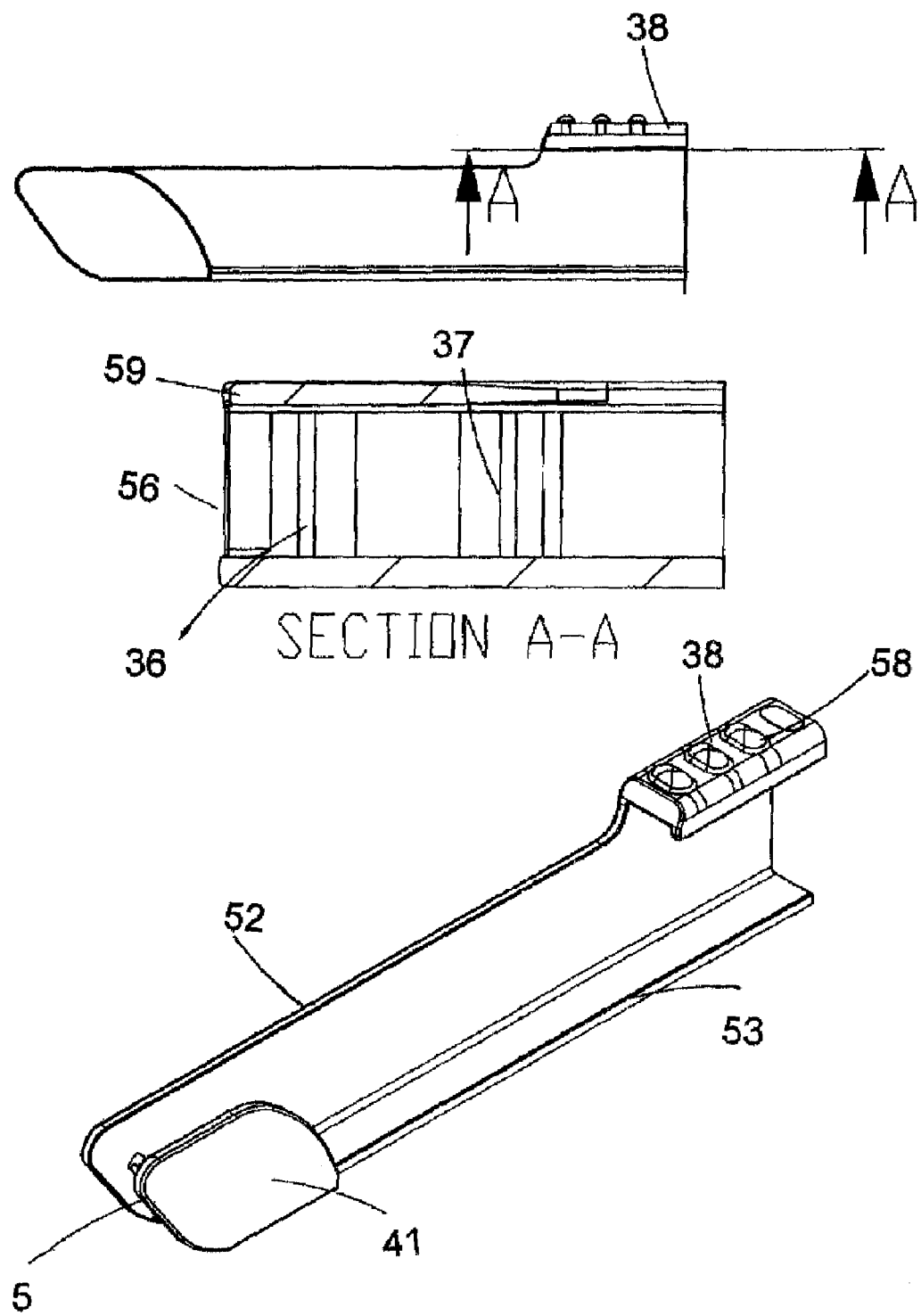
FIG. 4 includes a detail of the guide block and a frontal oblique view of the cover prior to assembly

Upper rail 17 has a linear travel rail 25 and interior upper shelf 8 along with leading edge portion 26, trailing edge buttress 27, leading edge buttress 29, and cover position securement means. In this invention, the securement means are leading edge glide inhibitor 30 and trailing edge glide inhibitor 28 along with the corresponding glide recesses 36 and 37. Glide inhibitor 28 and 30 are sloped detents that interface with corresponding glide recesses 36 and 37 located on the interior of guide block 38 as seen in FIG. 4. Interface between detents and recesses are such that moderate effort is needed to disengage mating parts. Guide block 38 has interior side 56 and exterior side 57 and guide lip 59. Interior side 56 has glide recesses 36 and 37 and exterior side 57 has gripping enhancing means 58 located on exterior side 57. In this invention, gripping enhancing means 58 entails a series of oval shaped detents whose purpose is to increase the surface area that will enable to the user to move glide block 38 along linear travel rail 25. Guide lip 59 interfaces with glide edge 60 which is the exterior facing side of linear travel guide 25. Guide lip 59 purpose is to hold guard 2 onto body 3 after assembly and during use. Guide lip 59 maintains proximal contact with edge 60 during sliding. An embodiment to this invention incorporates guide track 31 in place of, or in conjunction with, guide lip 59 located along the center axis of linear travel rail 25 having an front termination wall 34 abutting interior end of leading edge glide inhibitor 30 and a rear termination wall 35 at opposite of guide track 31 abutting interior end of trailing edge glide inhibitor 28. Guide track 31 is defined by guide track channel vertical walls 32 which recede into linear travel rail 25 and guide track channel bottom 33. In this invention, the guide track 31 recedes into linear travel rail 25 accepting guide rail button 34 in guide block 38 on guard 2. An alternate method, not shown, achieving similar results would entail having a protruding guide track 31 located upon linear travel rail 25, with a corresponding recess channel 34 in guide block 38. The purpose of the guide rail is to provide an extra measure of resistance preventing guard 2 from dislodging from body 3 during use.

FIG. 3 shows the method of installing scalpel 4 into body 3. Scalpel 4 is turned to approximately a 45 degree angle where bottom of scalpel 6 is placed in contact with bottom lower shelf 7 of body 3. Once scalpel is placed on lower shelf 7, scalpel 4 is rotated vertically snapping into placement in contact with upper shelf 8. One embodiment is the addition of spring 9 which is placed into spring slot 10. Spring 9 works in concert with positioning ribs 54 to supply upward force from the bottom of the scalpel 7, securing scalpel 7 into body 3 along ribs 54. This spring will sometimes be needed for handles that are smaller in stature enabling the device to accept a wider range of existing handles. Spring 9 material in this invention is metallic, but any material that would provide a spring like property could be used in this application. Removal of scalpel 7 is accomplished by the user inserting their finger into escapement hole 11, which is at the rear portion of body 3, and pushing the handle out of contact with lower shelf 7 and upper shelf 8.

Body 3 and guard 2 are assembled by placing the proximal end of guard 2 onto distal end of body 3 engaging sliding engagement member 53 onto lower slide wall 21 while guard 2 is held at a slight acute angle allowing guide block 38 not to interfere with leading edge portion 26 hereinafter guard 2 is pressed onto body 3 engaging guide block 38 onto linear travel guide 25 and guide lip 59 engages distal portion of linear travel rail 25. This operation is renewable and is designed for multiple assemblages and disassemblages.

Tip guard 5 is located on the distal end of guard 3. Tip guard 5 along with sliding engagement member 53 forms the channel which cradles the sharp portion of the sharp's device and prevents accidental contact with sharp. Tip guard 5 has an exterior tip guard portion 41 and interior tip guard portion 42. In one embodiment, attached to interior portion 42 is a blade detainment means. In this invention, blade retention device 45 is attached to interior portion 42. It is desirable to have the blade held between objects which precludes the chance of the blade ejecting into the air when the guard 2 is moved distally. Blade retention means 45 has two integral components, blade post 43 and tang groove 44. Medical Sharp 48 has a sharp distal point 49 and blade tang 46. Proximal end 46 is shaped into tang angle 47. Sharp 48 is held onto scalpel handle 50 by blade holder post 51 through an interference fit. Angle of blade retention device 45 matches that of tang angle 47 and is common throughout the medical industry.

Figure 5:
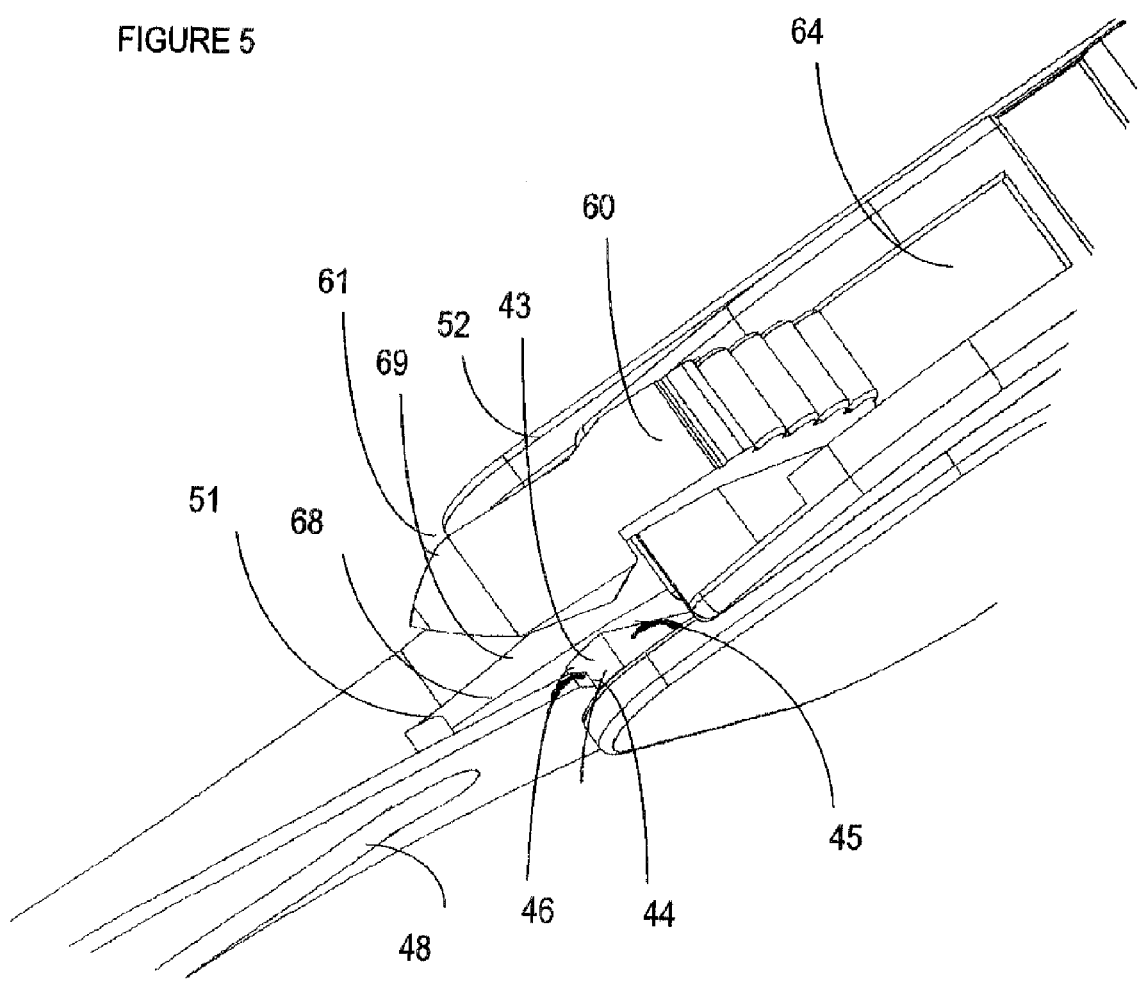
FIG. 5 is a detail of the hammer and the tang of the blade secured onto the blade containment slot.
Figure 6:
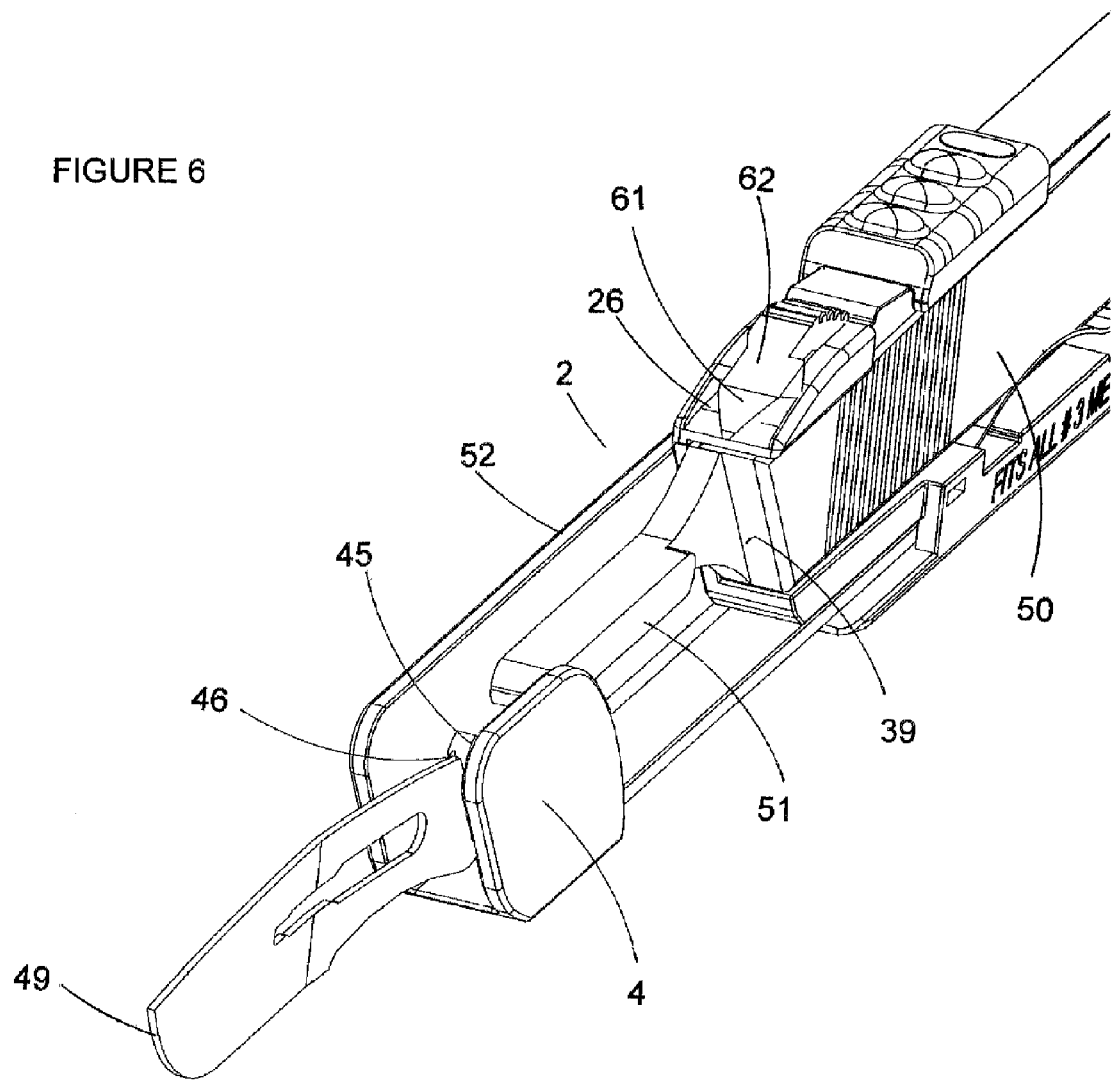
FIG. 6 shows the blade being pushed off of the handle by the extension of the cover from the body of the device.
Figure 7:
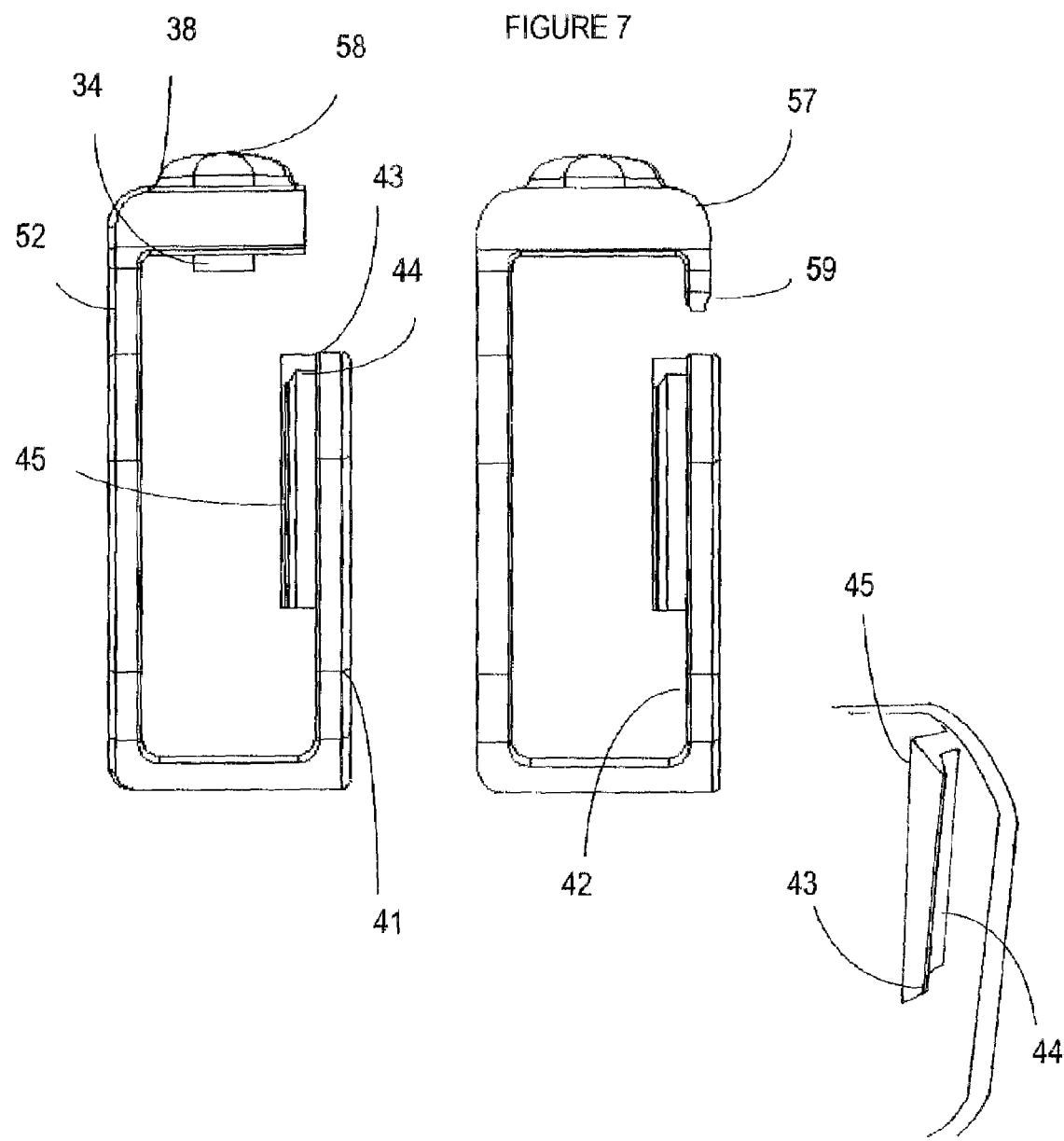
FIG. 7 is a frontal view of the cover detailing the position of the blade containment slot and the rail guide.
Figure 10:
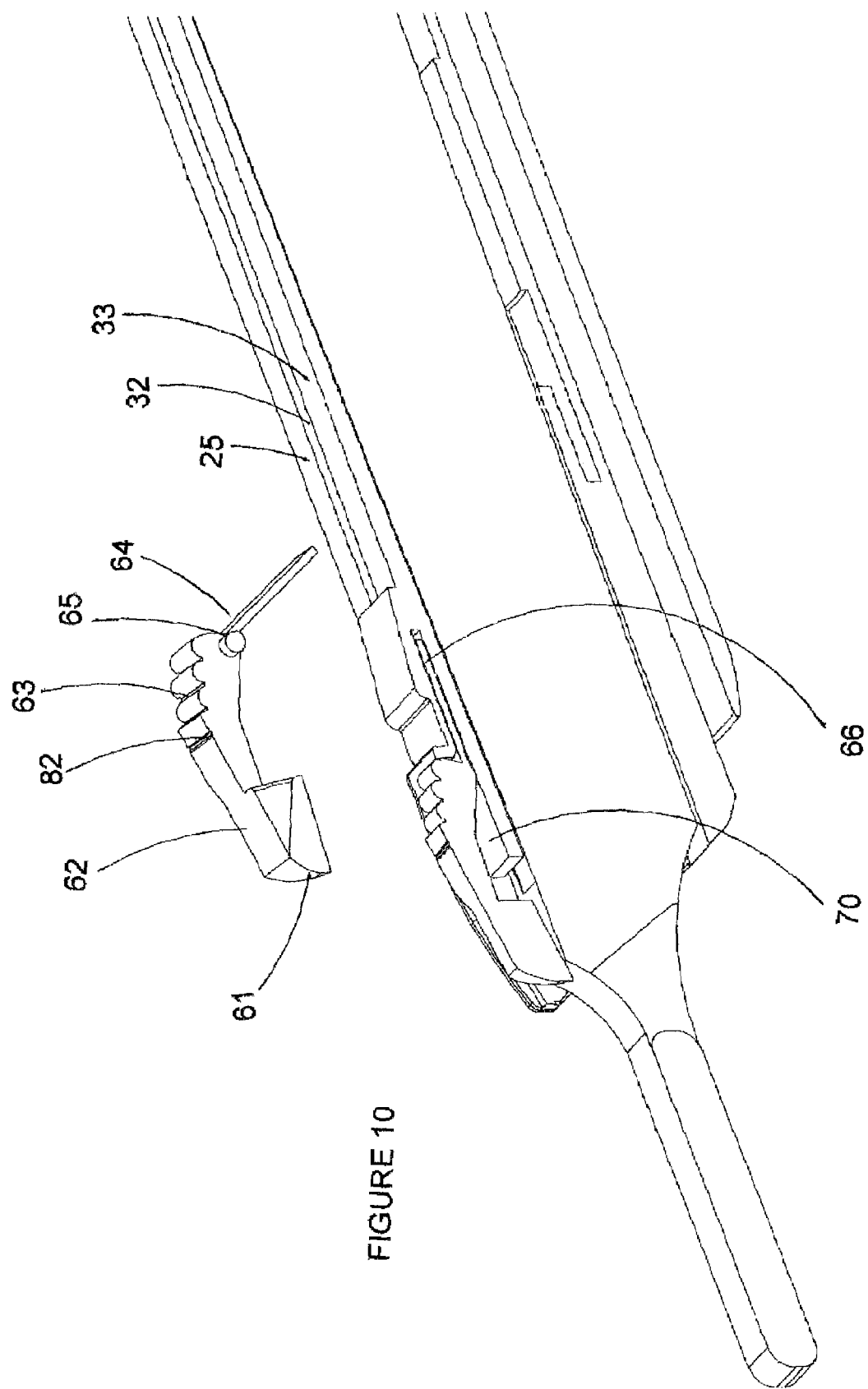
FIG. 10 shows the assembly of the hammer into the hammer containment slot
Figure 12:
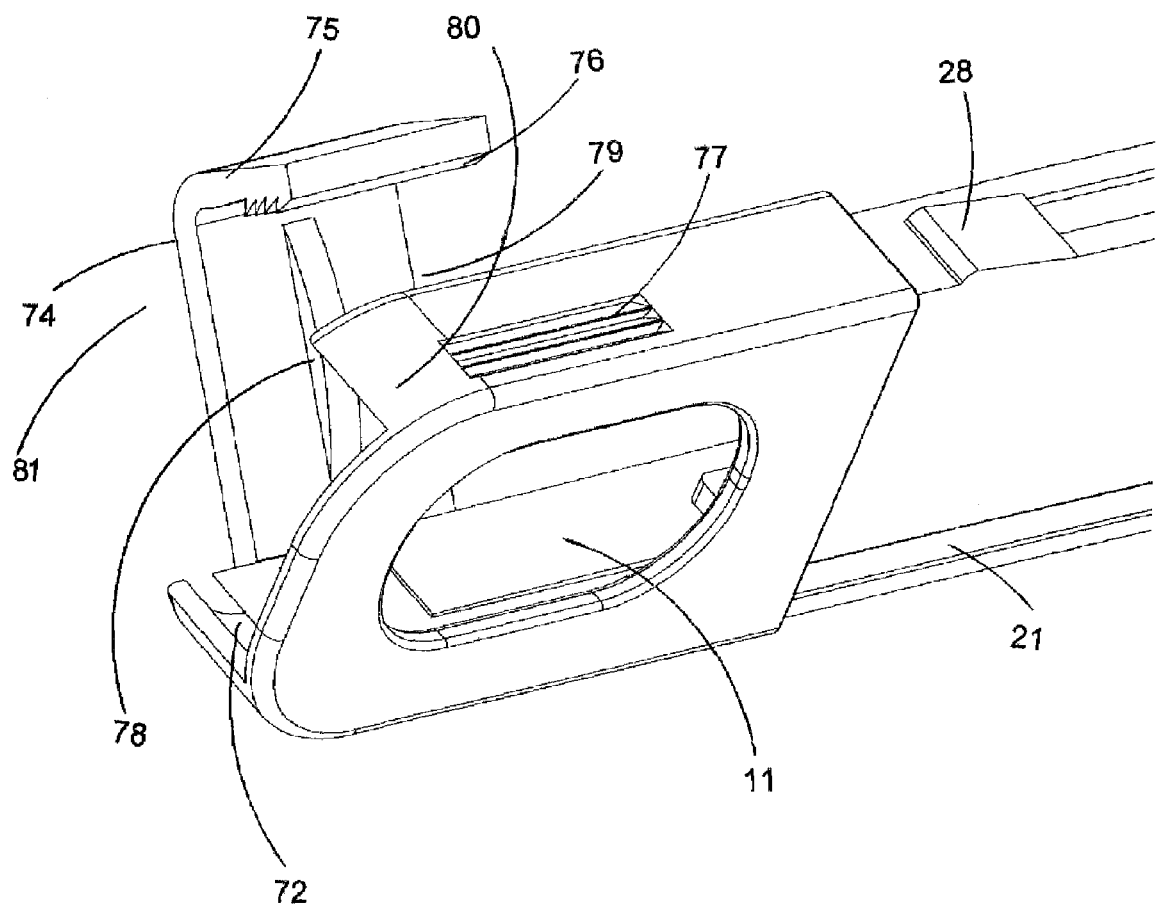
FIG. 12 is a view of the exterior side of the body from the rear portion detailing the cleat and the engagement of the gripping means.
Figure 13:
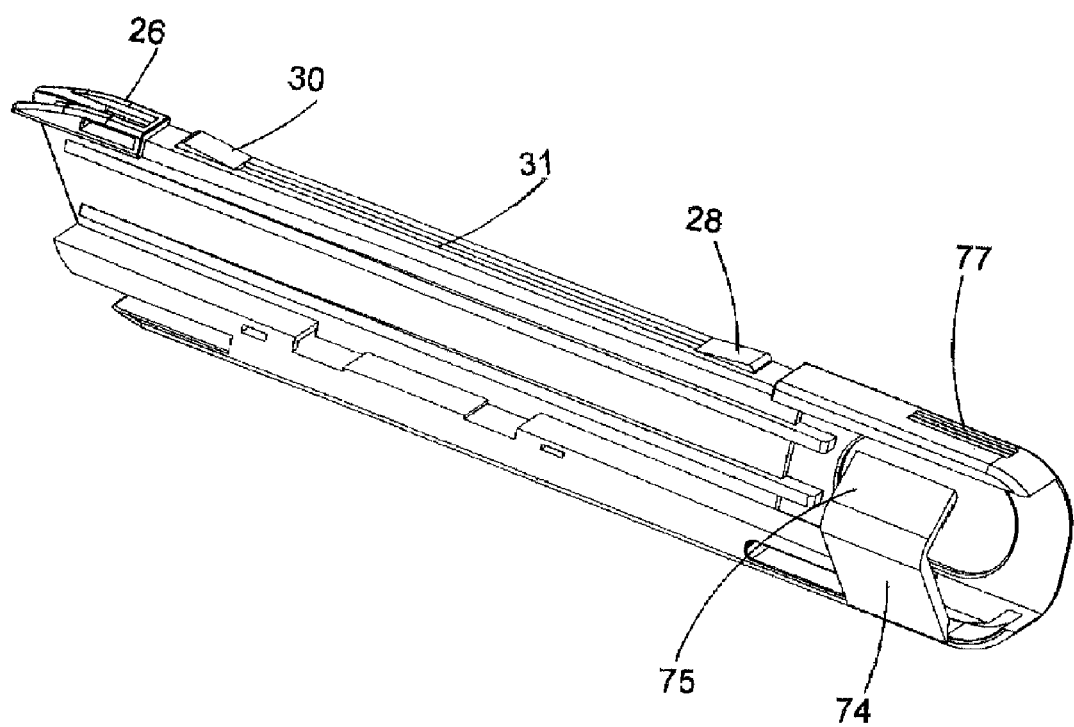
FIG. 13 is an oblique view of the body showing the cleat in the open position
Figure 14:
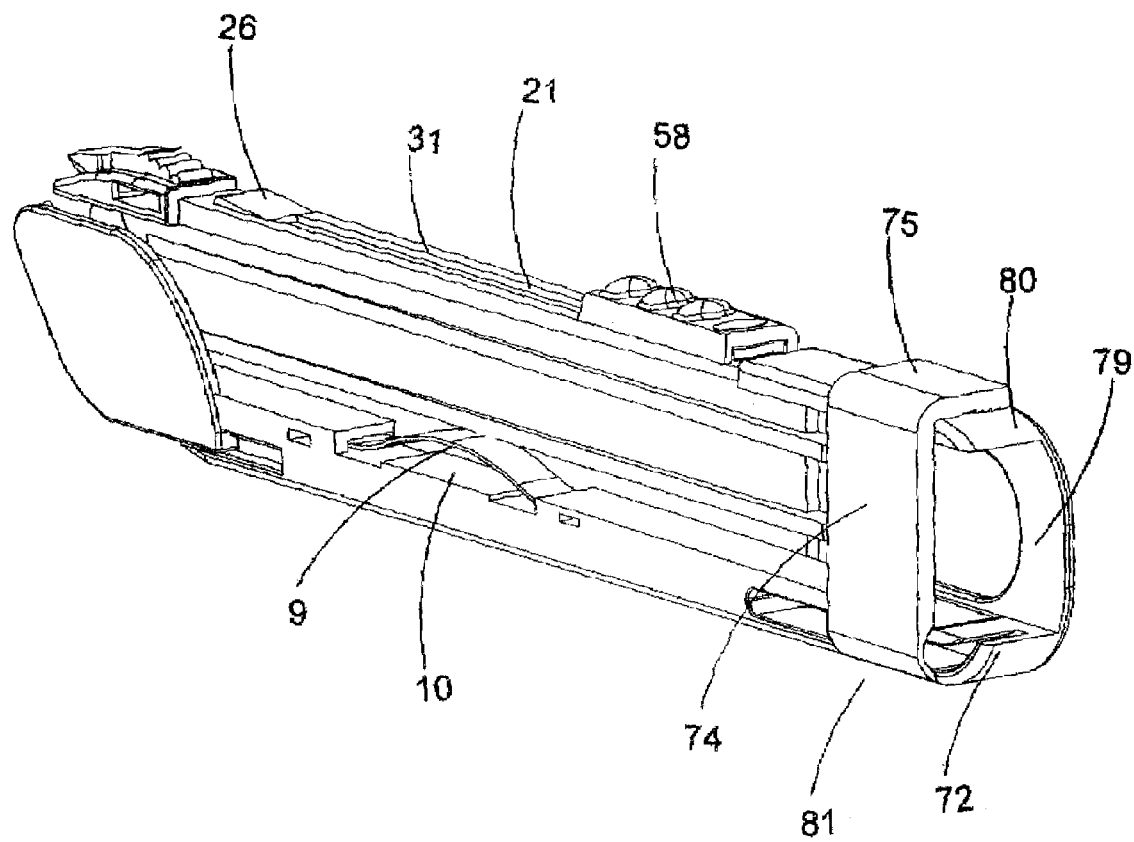
FIG. 14 is an oblique view of the body and guard in the open position with the cleat in the closed position.
Figure 15:
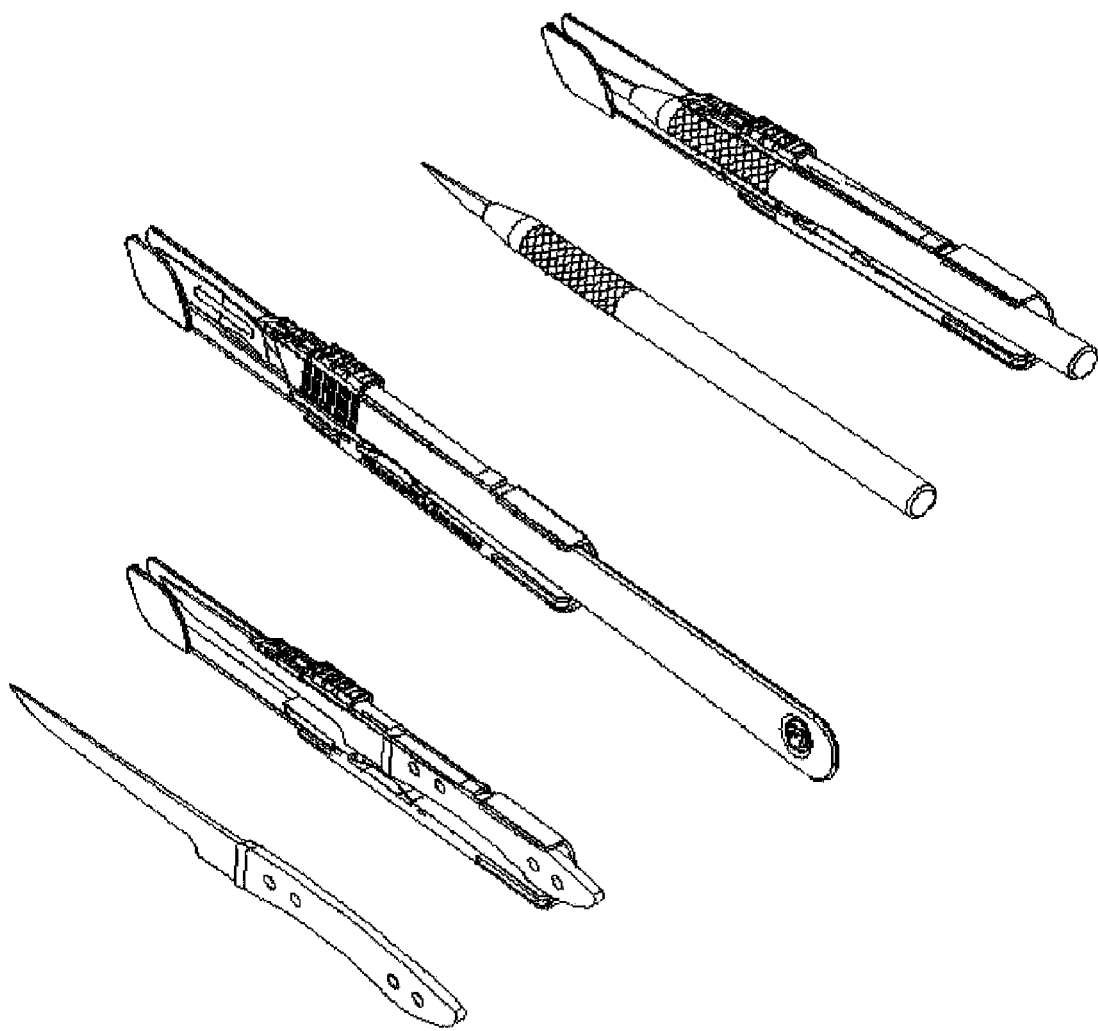
FIG. 15 shows the use of the device with a long handled scalpel without the use of the cleat, and also shows two other sharp devices, a paring knife and an X-Acto Style of hobby knife in the long handled style of the device.

Another embodiment of this invention details the use of hammer 82. Construction of hammer 82 is unique in that hammer 82 is created or formed in a pre-stressed condition such that the natural relaxed shape of hammer 82 forms a semi-circle or the letter "C". Hammer 82 contains hammer head 61, hammer arm 62, anti-slip means 63, slot pin 65 and spring 64. Hammer 60 is attached to an adapted leading edge portion 26 whereby guiding slot 67, hammer guide 70 and hammer spring slot 66 replace the smooth forward slope of leading edge portion 26. Guiding slot 67 is able to receive slot pin 65. Friction between pin 65 and slot 67 is sufficient to hold hammer 82 in place during use of device. Anti-slip means in this invention is a series of ridges 63 designed to maximize surface or gripping area so that the users hands will not slip off of the hammer. Any other form of structure who captures the same purpose would be within the spirit of these means. Due to hammer 82 being forced from the natural semi-circular position into the position of use shown in FIGS. 8 and 10, spring 64 stresses being in the flat condition. Due to the low modulus of elasticity of the material used, whether it is spring steel or polymer based, spring 64 will try to return itself into a semi-circular condition, thus creating frictional contact with the upper and lower walls of hammer spring slot 66, which prevents the accidental movement of the hammer when the user does not want the hammer to be in the forward position. Hammer arm 62 is long enough to position hammer head 61 into correct position prior to engagement. Hammer 82 slides along hammer guide from a rear proximal position abutting leading edge buttress 29 and a distal position where hammer is positioned over the blade tang 46. Due to the desire of hammer 82 to return to it's semi-circular condition, hammer head 61 and hammer arm 62 will arc downwardly toward the blade tang 46. Extent of travel of hammer 82 is dictated by length of slot 67 as detailed in FIG. 10. Hammer 82 serves to remove the blade tang 46 from blade holder post 51 by forcing its tetrahedronal shaped head 61 between the interior portion of tang 68 and blade holder wall 69. This invention uses a tetrahedronal shaped head to maximize the mechanical effort but other designs of the hammer are possible. FIG. 5 shows hammer 82 in it's forward position after the blade tang 46 has been removed from blade holder post 51 along with guard 2 being in the rear position. Upon disengagement of the blade tang 46 from post 51, blade tang 46 is captured by blade tang groove 44 and is held in place by blade post 43. Forward motion of guard 2 from the rear position will remove the rest of the blade from the blade holder post 51. As blade is captured between tang groove 44 and blade post 43 and interior tip guard portion 42, blade is held in a controlled environment preventing the violent expulsion of the blade from the holder due to stresses brought on by the interferences between the blade and the holder. This is detailed in FIG. 6.

Another embodiment is the addition of cleat 81. Cleat 81 is comprised of hinge 73, vertical support 74 and external top side 75. Removal of vertical wall 71 creates long handle opening 79 which is described about the radius of rear end 13 having an upper terminus 80 which is coplanar to upper shelf 8 and having a lower terminus 72 which is coplanar to lower shelf 7. Hinge 73 is created out of a thinning of material molded into the exterior side of body 3 closest to rear end 13. In this example of this device being made out of a thermoplastic, hinge 73 would be known to those in the art as a living hinge. Should this device be made of steel or similar ferrous metals, a suitable attachment of cleat 81 to body 3 would be a piano style hinge or the like. Opposite of exterior top side 75 is gripping means 76. In this example, gripping means 76 is a series of horizontal ridges which are right triangularly shaped which protruded from the surface. Gripping receiving means 77 are located on body 3 where they would directly interface with gripping means 76. Gripping receiving means 77 are always the mating or antithesis part to gripping means 76. An embodiment to this cleat, is the addition of pad 78, which provides extra resistive forces to handle 50 containing longer handles which would be able to generate larger amounts of torque due to their length, causing them to be expelled from body 3 more easily. User following insertion of handle into body 3, presses cleat 81 toward body 3 engaging gripping means and gripping receiving means.

What is claimed is:

1. A sharps blade protection device comprising
   a body portion having 3 vertical walls emanating from a planar surface, defining an exterior backside and interior open side, adapted to receive a sharp blade handle, said body having an open end and a distal closed end, a leading edge buttress and a trailing edge buttress, a long handle opening, a linear travel rail, said travel rail having a terminus at an open position abutting to said trailing edge buttress and a closed position abutting to leading edge buttress, a sharps handle escapement opening and a linear slide guide;
   a positioning means for securing said sharps blade handle to said interior side of said body;
   a guard operating in a parallel axis with said body and slidably attached to said body, said guard comprising a linear travel guide block, a lower sharps guard, a lateral sharp protection wall, a lateral tip guard and a sliding engagement member; and
   a cover position securement means where diametrically opposed surfaces on said linear travel rail and said linear travel guide block act in manners creating a positive securing at said open position and said closed position of said linear travel rail, preventing accidental dislodgement of said cover from said ends along said linear travel rail and providing tactile and auditory information to user of position of said linear travel guide block along said linear travel rail.

2. A sharps blade protection device as in claim 1 where positioning means have the resiliency to withstand more than 1 engagement/disengagement operation and with sufficient bias to engage said sharps handle preventing accidental dislodgement of said sharps handle from said body.

3. A sharps blade protection device as in claim 2 where positioning means include a spring.

4. A sharps blade protection device as in claim 2 where a cleat is used to secure handle of said sharp in place.

5. A sharps blade protection device as in claim 1 where linear travel guide block has anti-slip means attached to the exterior portion of said guide block.

6. A sharps blade protection device as in claim 1 where said body is shaped to receive handle of the object containing the sharp.

7. A sharps blade protection device as in claim 1 in which a guide track is superimposed upon said linear travel rail and a button whose shaped is diametrically opposed to shape of said guide track implanted onto said linear guide block.

8. A sharps blade protection device as in claim 1 in which opening of said linear slide guide is positioned such as to allow said guide to slide along said exterior backside of said body.

9. A sharps blade protection device as in claim 1 in which opening of said linear slide guide is positioned such as to allow said guide to slide along said interior open side of said body.

10. A sharps blade protection device comprising
a body portion having 3 vertical walls emanating from a planar surface, defining an exterior backside and interior open side, adapted to receive a sharp blade handle, said body having an open end and a distal closed end, a leading edge buttress and a trailing edge buttress, a long handle opening, a linear travel rail, said travel rail having a terminus at an open position abutting to said trailing edge buttress and a closed position abutting to leading edge buttress, a sharps handle escapement opening and a linear slide guide;
a disassociating member, attached appurtenant to said leading edge buttress on said body;
a positioning means for securing said sharps blade handle to area between said sides of said body;
a guard operating in a parallel axis with said body and slidably attached to said exterior of said body, said guard comprising a linear travel guide block, a lower sharps guard, a lateral sharp protection wall, a lateral tip guard and a sliding engagement member; and
a cover position securement means where opposing surfaces on said linear travel rail and said linear travel guide block act in diametrically opposed manners creating a positive securing at said open position and said closed position of said linear travel rail, preventing accidental dislodgement of said cover from said ends along said linear travel rail and providing tactile and auditory information to user of position of said linear travel guide block along said linear travel rail.

11. A sharps blade protection device as in claim 10 where said disassociating member is positioned above the blade of said sharp and where said disassociating member acts in a descending plane causing disassociation between the sharp and the sharp handle.

12. A sharps blade protection device as in claim 10 where said disassociating member is constructed in a manner where said disassociating member is in a stressed state when placed in a level position where each end is in the horizontal plane.

13. A sharps blade protection device as in claim 10 where disassociating member moves proximal end of said sharp onto a three sided detainment means prior to release to originating position of said disassociating member and where detainment means are located such that proximal end of sharp is not exposed while detained.

14. A sharps blade protection device as in claim 13 where user can remove said detained sharp from said handle in a single handed operation while said proximal end of sharp is detained during deracination of said sharp from said handle.

15. A sharps blade protection device as in claim 10 where said body is shaped to receive handle of the object containing the sharp.

16. A sharps blade protection device as in claim 10 in which a guide track is superimposed upon said linear travel rail and a button whose shaped is diametrically opposed to shape of said guide track implanted onto said linear guide block.

17. A sharps blade protection device as in claim 10 where positioning means have the resiliency to withstand more than 1 engagement/disengagement operation and with sufficient bias to engage said sharps handle preventing accidental dislodgement of said sharps handle from said body.

18. A sharps blade protection device as in claim 17 where positioning means include a spring.

19. A sharps blade protection device as in claim 17 where a cleat is used to secure handle of said sharp in place.

20. A sharps blade protection device as in claim 10 where linear travel guide block has anti-slip means attached to the exterior portion of said guide block.

21. A sharps blade protection device as in claim 10 in which opening of said linear slide guide is positioned such as to allow said guide to slide along said exterior backside of said body.

22. A sharps blade protection device as in claim 10 in which opening of said linear slide guide is positioned such as to allow said guide to slide along said interior open side of said body.

* * * * *